(12) United States Patent
Su et al.

(10) Patent No.: US 8,828,434 B2
(45) Date of Patent: Sep. 9, 2014

(54) NANOCOMPOSITE HYDROGEL AND METHOD FOR PREPARING IT, FOR INDUSTRIAL AND MEDICAL APPLICATIONS

(75) Inventors: Shunxing Su, Richmond (CA); Wadood Y. Hamad, Vancouver (CA)

(73) Assignee: FPInnovations, Pointe-Claire, Quebec (CA)

(*) Notice: Subject to any disclaimer, the term of this patent is extended or adjusted under 35 U.S.C. 154(b) by 123 days.

(21) Appl. No.: 13/010,020

(22) Filed: Jan. 20, 2011

(65) Prior Publication Data

US 2011/0182990 A1    Jul. 28, 2011

Related U.S. Application Data

(60) Provisional application No. 61/282,319, filed on Jan. 22, 2010.

(51) Int. Cl.
*A61K 9/14* (2006.01)
*A61F 13/15* (2006.01)
*A61F 13/20* (2006.01)
*C08J 3/24* (2006.01)
*A61L 27/48* (2006.01)
*C08J 5/00* (2006.01)
*A61L 15/22* (2006.01)
*A61L 15/28* (2006.01)
*B82Y 30/00* (2011.01)
*A61L 15/24* (2006.01)

(52) U.S. Cl.
CPC .. *C08J 3/24* (2013.01); *A61L 27/48* (2013.01); *C08J 5/005* (2013.01); *A61L 2400/12* (2013.01); *A61L 15/225* (2013.01); *A61L 15/28* (2013.01); *B82Y 30/00* (2013.01); *A61L 15/24* (2013.01)

USPC .......................................... 424/484; 604/367

(58) Field of Classification Search
None
See application file for complete search history.

(56) References Cited

U.S. PATENT DOCUMENTS 4,194,877 A * 3/1980 Peterson ........................... 8/526
2005/0037082 A1   2/2005 Wan et al.

FOREIGN PATENT DOCUMENTS

GB          1512325       6/1978
RU          2298022       4/2007

OTHER PUBLICATIONS

Cosentino et al, New nanostructured cellulose materials for the filtration of pollutants and for the adsorption of dyes, 2008, NSTI Nanotech, Nanotechnology Conference and Trade Show, Technical Proceedings, Boston, MA, United States, Jun. 1-5, 2008, vol. 2, pp. 110-113, 1 page only (Abstract only).*
Zhou, Chengjun et al., "Application of rod-shaped cellulose nanocrystals in polyacrylamide hydrogels", Journal of Colloid and Interface Science, vol. 353, p. 116-123 (2011). entire document.

(Continued)

*Primary Examiner* — Trevor Love
(74) *Attorney, Agent, or Firm* — Norton Rose Fulbright Canada LLP (57) ABSTRACT

Nanocrystalline cellulose (NCC) is employed as the cross-linker and reinforcement domain for developing nanocomposite hydrogels possessing high strength and improved diffusion property; the resulting nanocomposite hydrogels are shown to have high mechanical properties, reversible swelling ability, and are biodegradable and biocompatible; the approach relies on free radical polymerization to form the hydrogels using a variety of hydrophilic vinyl monomers. These hydrogels are suitable for developing highly absorbent hygiene products, as well as for applications in medicine, engineering materials and sensors.

20 Claims, 5 Drawing Sheets

(56) References Cited

OTHER PUBLICATIONS

Goetz, Lee et al., "A novel nanocomposite film prepared from crosslinked cellulosic whiskers", Carbohydrate Polymers, vol. 75, p. 85-89 (2009). entire document.

International Search Report, PCT/CA2011/000071, Apr. 7, 2011.

Yoshida, R., Design of functional polymer gels and their application to biomimetic materials, Current Organic Chemistry 2005, 9, (16), 1617-1641.

Tokarev, I.; Minko, S., Stimuli-responsive hydrogel thin films. Soft Matter 2009, 5, (3), 511-524.

Peppas, N. A.; Hilt, J. Z.; Khademhosseini, A.; Langer, R., Hydrogels in biology and medicine: From molecular principles to bionanotechnology. Advanced Materials 2006, 18, (11), 1345-1360.

Hoare, T. R.; Kohane, D. S., Hydrogels in drug delivery: Progress and challenges. Polymer 2008, 49, (8), 1993-2007.

Richter, A.; Paschew, G.; Klatt, S.; Lienig, J.; Arndt, K. F.; Adler, H. J. P., Review on hydrogel-based pH sensors and microsensors. Sensors 2008, 8, (1), 561-581.

He, C. L.; Kim, S. W.; Lee, D. S., In situ gelling stimuli-sensitive block copolymer hydrogels for drug delivery. Journal of Controlled Release 2008, 127, (3), 189-207.

Calvert, P., Hydrogels for Soft Machines. Advanced Materials 2009, 21, (7), 743-756.

Okumura, Y.; Ito, K., The polyrotaxane gel: A topological gel by figure-of-eight cross-links. Advanced Materials 2001, 13, (7), 485-487.

Haraguchi, K., Nanocomposite hydrogels. Current Opinion in Solid State & Materials Science 2007, 11, (3-4), 47-54.

Gong, J. P.; Katsuyama, Y.; Kurokawa, T.; Osada, Y., Double-network hydrogels with extremely high mechanical strength. Advanced Materials 2003, 15, (14), 1155-1158.

Haraguchi, K.; Takehisa, T.; Fan, S., Effects of clay content on the properties of nanocomposite hydrogels composed of poly(N-isopropylacrylamide) and clay. Macromolecules 2002, 35, (27), 10162-10171.

English language translation of RU 2298022, dated 2007.

* cited by examiner

NANOCOMPOSITE HYDROGEL AND METHOD FOR PREPARING IT, FOR INDUSTRIAL AND MEDICAL APPLICATIONS

CROSS-REFERENCE TO RELATED APPLICATION

This application claims the benefit under 35 USC 119(e) of U.S. Provisional Application Ser. No. 61/282,319, filed Jan. 22, 2010.

BACKGROUND OF THE INVENTION

1. Field of the Invention

The invention generally relates to novel nanocomposite hydrogels, and a method of preparing nanocomposite hydrogels, and more specifically to the application of nanocrystalline cellulose (NCC) as both crosslinker and reinforcement domain in polymer hydrogels. The approach relies on free radical polymerization to form the hydrogels using a variety of hydrophilic vinyl monomers. This invention is suitable for developing applications in medicine, engineering materials, sensors, and consumer products (e.g. highly absorbent hygiene products).

2. Description of the Prior Art

Polymer hydrogels are crosslinked hydrophilic polymer networks that swell when absorbing large amounts of water. Hydrogels have been investigated extensively in the past several decades for a large variety of applications, such as drug delivery, tissue engineering, stimuli-responsive sensor, etc.[1-6] In general, hydrogels are soft and brittle. However, there are applications that require significant mechanical loads, for example, medical implants, and some electrochemical devices.[7] Designing hydrogels for a multitude of novel and existing applications require them to possess sufficient mechanical strength, as well as retain their original properties, such as stimuli responsiveness and fast diffusion.

In nature, there are many hydrogels with very high mechanical strengths.[7] Many marine plants, such as kelp, are polysaccharide hydrogels reinforced with polymeric or inorganic fibres. In the human body, cartilage, cornea, and the dermis are all fibre reinforced hydrogels. These fibres reinforce the hydrogels by acting as the load-bearing components.

Recently, three new hydrogels with good mechanical properties have been reported: topological gels, nanocomposite gels, and double network gels. The topological gels have figure-of-eight crosslinkers which are able to slide along the polymer chains.[8] As a result, these gels are highly stretchable and can absorb large amounts of water. For nanocomposite gels, the polymer chains are crosslinked by nanoparticles, for instance, inorganic clay, instead of organic crosslinking agents.[9] The nanocomposite hydrogels are also highly stretchable and have very good tensile strength. Double network hydrogels have two interpenetrating polymer networks: one is a highly crosslinked rigid polymer matrix, while the other one is a loosely crosslinked flexible polymer matrix.[10] These double network hydrogels have very high hardness and toughness.

SUMMARY OF THE INVENTION

It is an object of this invention to provide a novel nanocomposite hydrogel.

It is another object of this invention to provide a new method of preparing a nanocomposite hydrogel.

In one aspect of the invention, there is provided a nanocomposite hydrogel comprising a hydrophilic polymer crosslinked by a crosslinker comprising nanocrystalline cellulose (NCC).

In another aspect of the invention, there is provided a method of preparing a nanocomposite hydrogel comprising: polymerizing a hydrophilic monomer to form a hydrophilic polymer in the presence of a crosslinker for said polymer, which comprises nanocrystalline cellulose (NCC).

In other aspects of the invention, there is provided novel devices, for example medical devices and absorbent hygiene devices formed from the nanocomposite hydrogel of the invention.

In still other aspects of the invention, there is provided use of the nanocomposite hydrogel of the invention as an engineering material.

In still other aspects of the invention, there is provided use of the nanocomposite hydrogel of the invention as a drug delivery system in medical applications.

In still other aspects of the invention, there is provided use of the nanocomposite hydrogel of the invention as a stimuli-responsive sensor.

In still other aspects of the invention, there is provided use of the nanocomposite hydrogel of the invention for medical implants.

In still other aspects of the invention, there is provided use of the nanocomposite hydrogel of the invention in tissue engineering.

DETAILED DESCRIPTION OF THE INVENTION

The nanocomposite hydrogel comprises a hydrophilic polymer, in particular a hydrophilic polymer derived from polymerization of a hydrophilic vinyl monomer, which polymer is crosslinked by a crosslinker comprising nanocrystalline cellulose (NCC).

Nanocrystalline cellulose (NCC) is extracted as a colloidal suspension by acid hydrolysis of typically chemical wood pulps, but other cellulosic materials, such as bacteria, cellulose-containing sea animals (e.g. tunicate), or cotton can be used. NCC is constituted of cellulose, a linear polymer of $\beta(1\rightarrow 4)$ linked D-glucose units, the chains of which arrange themselves to form crystalline and amorphous domains. NCC obtained via hydrolytic extraction has a degree of polymerization (DP) in the range $90 \leq DP \leq 110$, and 3.7-6.7 sulphate groups per 100 anhydroglucose units. NCC comprise crystallites whose physical dimension ranges between 5-10 nm in cross-section and 20-100 nm in length, depending on the raw material used in the extraction. These charged crystallites can be suspended in water, or other solvents if appropriately derivatized, or self assemble to form solid materials via air, spray- or freeze-drying. When dried, NCC forms an agglomeration of parallelepiped rod-like structures, which possess cross-sections in the nanometer range (5-20 nm), while their lengths are orders of magnitude larger (100-1000 nm) resulting in high aspect ratios. NCC is also characterized by high crystallinity (>80%, and most likely between 85 and 97%) approaching the theoretical limit of the cellulose chains. Hydrogen bonding between cellulose chains can stabilize the local structure in NCC, and plays a key role in the formation of crystalline domains. Crystallinity, defined as the crystalline fraction of the sample, strongly influences the physical and chemical behaviour of NCC. For example, the crystallinity of NCC directly influences the accessibility for chemical derivatization, swelling and water-binding properties.

In particular, the crosslinker comprises a modified NCC in which a modifier has a first functional group coupled with a hydroxyl group of the NCC, and a second functional group coupled to the polymer.

The modifier is suitably a vinyl monomer having a functional group, by way of example there may be mentioned glycidyl methacrylate. Based on their molecular structures, a group of chemicals can appropriately be selected to function as modifiers for the NCC. Some examples are: trimethylsilyl methacrylate, 2-(trimethylsilyloxy)ethyl methacrylate, 2-aminoethyl methacrylate, 2-isocyanatoethyl methacrylate, 2-chloroethyl acrylate, 3-(trimethoxysilyl)propyl acrylate, glycidyl acrylate, vinyl isocyanate, 2-aminoethyl vinyl ether, and vinyltrimethoxysilane. Suitable hydrophilic monomers include, by way of example, acrylic acid, acrylamide (AM), vinyl-2-pyrrolidinone. N-isopropylacrylamide (NIPAM), and N-vinylformamide (NVF). The following group of hydrophilic monomers can also be identified for polymer formation. α-ethylacrylic acid, methacrylic acid, 2-acrylamido-2-methyl-1-propanesulfonic acid, hydroxypolyethoxy (10) allyl ether, 2-hydroxyethyl acrylate, 3-sulfopropyl acrylate potassium salt, poly(ethylene glycol) acrylate, tetrahydrofurfuryl acrylate, and methacrylamide. Furthermore, in principle all of the aforementioned monomers can also be chosen as comonomers, so that the hydrophilic polymer is a hydrophilic copolymer, and hence as suitable combinations for the copolymerization reaction. Suitable comonomer combinations for copolymerization to produce the hydrophilic polymer are for example, acrylamide and acrylic acid, acrylamide and methacrylic acid, N-isopropylacrylamide and acrylic acid, N-isopropylacrylamide and poly(ethylene glycol) acrylate, and poly(ethylene glycol) acrylate and acrylamide.

Thus the polymerization of the hydrophilic vinyl monomer can be a homopolymerization of a vinyl monomer or a homopolymerization of a vinyl monomer and a comonomer.

In the case of a copolymerization, in order to make a good hydrogel, hydrophilic monomers and hydrophilic comonomers are employed to form the crosslinked network which should be able to swell in aqueous media.

It will be understood that the first functional group may be any group that will react or couple with a group on the NCC such as a hydroxyl group, to couple the modifier to the NCC; and the second functional group may be any group that will react or couple with a group on the polymer or the monomer forming the polymer. Persons in the art will be able to select modifiers with suitable functional groups for coupling with the NCC and hydrophilic polymer or monomer for forming such polymer. Similarly persons in the art will be able to select monomers for the polymer formation having suitable functional groups for coupling with the second functional group of a modifier.

It will be understood that while reference is made to a monomer for polymer formation, it is within the invention to additionally employ comonomers so as to produce crosslinked copolymers rather than crosslinked homopolymers; in such case the comonomers need not participate in the crosslinking although this is also possible. In this way hydrogels of a variety of desired characteristics can be produced by selection of hydrophilic monomers, modifiers and optional comonomers.

Furthermore a method for the preparation of nanocomposite hydrogels with nanocrystalline cellulose (NCC) as the crosslinker and reinforcement domain is provided. Each NCC nanoparticle attaches to at least two units of the modifier. The NCC is expected to be completely randomly distributed within the hydrogel structure. The prepared hydrogel has high mechanical strength while maintaining the original properties. Compared to clay-based nanocomposite hydrogels, NCC is biodegradable and biocompatible. This makes the NCC-based hydrogels more promising for the medical related applications since biodegradability and biocompatibility are critical. The preparation of the NCC nanocomposite hydrogel involves a two step process. The first step is NCC modification to render it a suitable crosslinker, and the second is in situ polymerization of hydrophilic vinyl monomers with the modified NCC to make nanocomposite hydrogels.

Hydrogels of the invention possess excellent mechanical strength while retaining their original properties, such as stimuli responsiveness and fast diffusion, and as such can be developed in a great number of hydrogel-based new applications.

In specific embodiments of this invention, free radical polymerization is used for forming nanocrystalline (NCC) based nanocomposite hydrogels. A variety of hydrophilic vinyl monomers are suitable, such as acrylic acid, acrylamide (AM), vinylpyrrolidone, N-isopropylacrylamide (NIPAM), N-vinylformamide (NVF) etc. Since there is no crosslinking spot on NCC during the polymerization, NCC must first be modified to function as a crosslinker. The modification is performed by following a procedure whereby a vinyl monomer with functional groups, for example glycidyl methacrylate (GMA), is used to react with the hydroxyl groups on NCC, which results in NCC coupled with the methacrylate group. Then, the nanocomposite hydrogel is prepared by using the modified NCC and hydrophilic monomers, such as acrylamide, initiated with free radical initiators, such as potassium persulfate. Following the procedure of this invention, nanocomposite hydrogels prepared from the modified NCC are much stronger than the hydrogels prepared from a regular organic crosslinker, for instance, N,N'-Methylenebisacrylamide (BIS).[11] The water swelling ability of the resulting nanocomposite hydrogel is reversible, which indicates that the diffusion property of the hydrogel is retained while the mechanical properties are enhanced. The molecular weight or polymer chain length between NCC particles can be controlled by two principal factors: (i) NCC concentration, and (ii) the density of grafted modifiers on the NCC surface. The higher the NCC concentration and the density of grafted modifier on NCC surface are, the shorter the polymer chains will be. Conversely, the lower the NCC concentration and the density of grafted modifier on NCC surface are, the longer the polymer chains become. However, the NCC concentration can also affect the mechanical strength of the resulting hydrogel.

The above described method is not limited to the use of acrylamide as the monomer. The choice of different monomers is dependent on the final application. For different monomer systems, the nanocomposite hydrogels can be pH responsive, temperature sensitive, electrochemically sensitive, etc. Enhancing the mechanical strength will widen the potential application for hydrogels into a wide range of engineering materials and medical systems.

Detailed description of the specific steps which may be employed for the preparation of NCC-based nanocomposite hydrogels is described below.

Surface modification of NCC with a vinyl monomer possessing suitable functional groups: NCC suspension in water with a certain concentration, for example 4.38% wt, is used. The pH of the NCC suspension is adjusted to neutral, and the NCC suspension is then dried using an appropriate technique, for instance spray or freeze drying. Several grains of freeze dried NCC, typically 1 to 10 g, for example 5 g is resuspended in 50 to 500 ml of an appropriate solvent, for example dimethyl sulfoxide (DMSO), preferably 100 ml, with stirring for 10 mins to 4 hours until NCC is fully suspended. The choice of solvent is only limited by the fact that the NCC suspension must be fully dispersed. The NCC suspension is then ultrasonicated for 10 to 60 mins. Desired amount of a catalyst, for example 1 g of 4-Dimethylaminopyridine (DMAP), is added into the suspension, and the suspension is further bubbled with nitrogen for 10 to 60 mins to get rid of dissolved oxygen. The reaction is started by introducing the required amount, for instance 0.73 g, of a suitable vinyl monomer with functional groups, for example glycidyl methacrylate (GMA), into the suspension. The reaction can be performed at any temperature ranging from room temperature up to the degradation temperature of NCC; 50° C. is used in this case. The reaction time can range from 4 hours to several days, and 48 hours is applied here. The reaction time, temperature, ratio of GMA to NCC will determine the modification degree. After the reaction, some deionized (DI) water, 100 ml in this case, is introduced into the suspension and the pH of the system is adjusted to 7-8. The obtained suspension is dialyzed against DI water for 3 to 10 days, 7 days in this case. After dialysis, the suspension is ultrasonicated for 30 mins and filtered through, for example, Whatman No. 42 filter paper. Finally, the pH of the modified NCC suspension is adjusted to 7-8 and freeze dried.

Preparation of NCC-based nanocomposite hydrogels: The calculated amount of modified NCC and acrylamide are dissolved in DI water while stirring until fully dissolved, typically 10 mins to 60 mins, and then ultrasonicated for 10 to 30 mins. The suspension is then filtered through a 0.45 μm needle filter. The desired amount of a suitable catalyst, for instance N,N,N',N'-Tetramethylethylenediamine (TEMED), to assist with the generation of free radicals from the initiator is added to the NCC suspension, and the suspension is bubbled with nitrogen for at least 30 mins. The calculated amount of a suitable initiator, for example potassium persulfate (KPS), is dissolved in DI water and bubbled with nitrogen at the same time. To start the reaction, the KPS solution is introduced to the NCC suspension in an ice-water bath. The in situ free-radical polymerization is allowed to proceed at room temperature for 1 to 5 days, for example 2 days, until the reaction is finished in nitrogen atmosphere. The molar ratio of the monomer (acrylamide), initiator (KPS), and catalyst (TEMED) is kept constant in this specific sample at 381:1:2.35. Different NCC to acrylamide ratios can used to optimize the effect of NCC concentration on nanocomposite hydrogel mechanical properties. The molar ratio of other reactants can also be adjusted within a reasonable range to control the properties of the prepared NCC hydrogels.

TABLES

TABLE 1

Size and surface charge of modified NCC prepared using the indicated conditions.

| Sample Number | A | B | C | D | NCC |
|---|---|---|---|---|---|
| Reaction conditions | NCC:GMA weight ratio 1:0.146, 48 hours at room temp. | NCC:GMA weight ratio 1:0.146, 24 hours at 50° C. | NCC:GMA weight ratio 1:0.146, 48 hours at 50° C. | NCC:GMA weight ratio 1:0.292, 48 hours at 50° C. | |
| Diameter (nm) | 37.7 ± 1.3 | 37.9 ± 1.1 | 36.6 ± 0.7 | 38.4 ± 1.0 | 45.5 ± 1.2 |
| Surface charge (electrophoretic mobility $m^2/(V \cdot s)$) | −3.217 ± 0.253 | −3.335 ± 0.208 | −3.941 ± 0.366 | −3.344 ± 0.29 | −4.439 |

TABLE 2

Swelling ratios of NCC-based nanocomposite and BIS-based hydrogels.

| | Samples | | | | | |
|---|---|---|---|---|---|---|
| | $1.33 \times 10^{-5}$ mol/g Am BIS | $2.66 \times 10^{-5}$ mol/g Am BIS | $6.66 \times 10^{-5}$ mol/g Am BIS | 10 wt % NCC on Am | 20 wt % NCC on Am | 50 wt % NCC on Am |
| Swelling ratio | 2.70 ± 0.11 | 2.35 ± 0.05 | 1.88 ± 0.01 | 4.15 ± 0.04 | 3.886 ± 0.13 | 2.23 ± 0.21 |

Example 1

Figure 1:
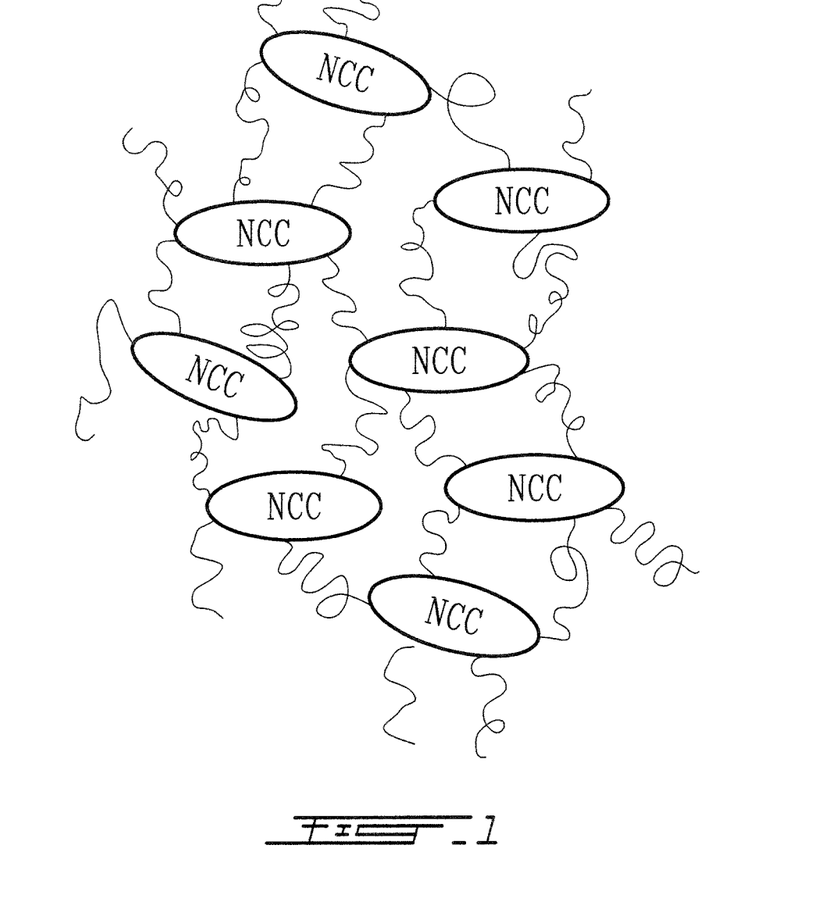
FIG. 1: is a schematic of how NCC functions as a crosslinker in the described nanocomposite hydrogels. Each nanoparticle attaches to at least two units of the modifier. The NCC is expected to be completely randomly distributed within the hydrogel structure.
Figure 2:
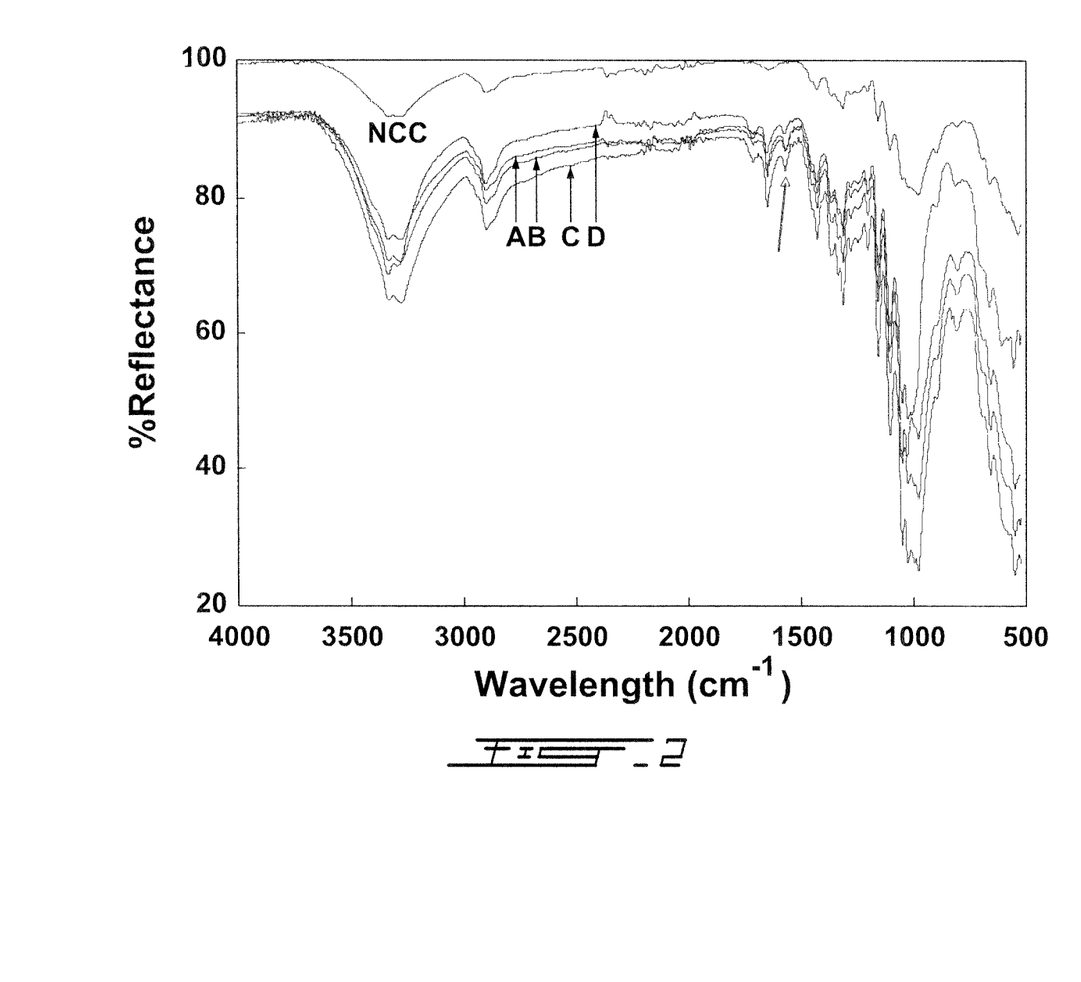
FIG. 2: is an FT-IR spectra of modified NCC according to the conditions described in Table 1.

The modification of NCC by GMA is controlled using different reaction conditions. It is illustrated in Table 1 that the surface charge of the modified NCC is decreased compared to the original NCC. Moreover, the modified NCC becomes smaller in size than the original NCC. This is likely because the catalyst, DMAP, is a base, which will possibly hydrolyze the NCC to make it smaller and decrease the surface charge. To confirm the grafting of GMA onto NCC, Fourier transform infra-red (FT-IR) examination is carried out to check the modified NCC samples. As demonstrated in FIG. 2, the peak at about 1720 cm$^{-1}$ represents the vibration of carbonyl group on methacrylate, which indicates that the methacrylate group is grafted onto NCC.

Example 2

The mechanical properties of the hydrogels can be analyzed using an Instron, or any other, tensile testing machine at an extension rate of 100 mm/min. The gauge length was set to 30 mm, and the test specimen is a solid cylinder with a diameter of 11.46 mm. The initial cross section is used to calculate the tensile strength and modulus.

Figure 3:
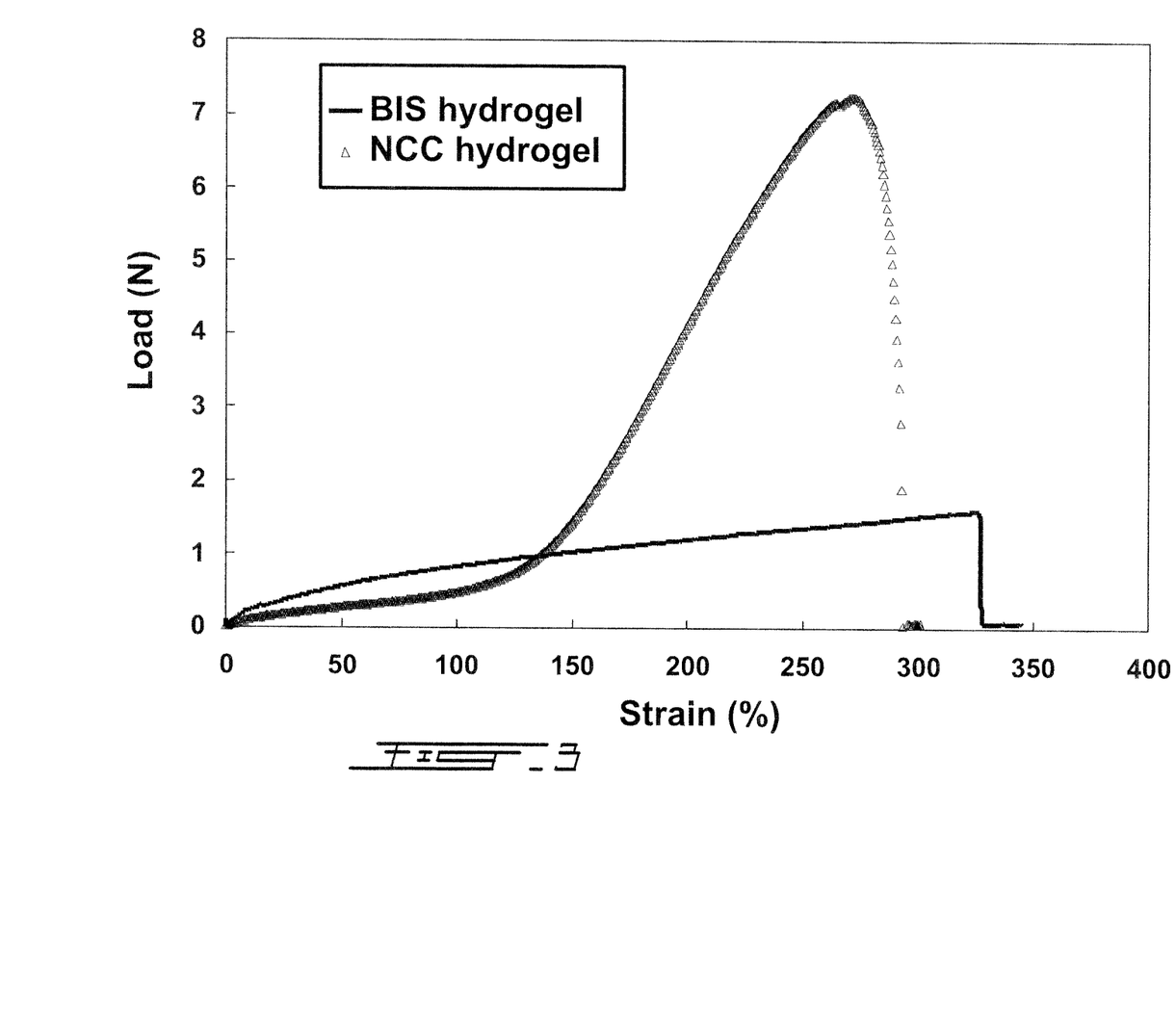
FIG. 3: is a plot showing the tensile behaviour of NCC-based nanocomposite (open triangles) and BIS-based (solid line) hydrogels.

FIG. 3 displays typical tensile responses of (1) NCC-based nanocomposite hydrogel prepared according to this invention, and (2) hydrogel prepared using an organic crosslinker, BIS. The NCC-based nanocomposite hydrogel exhibits a characteristically different behaviour to that of hydrogels produced using organic crosslinkers. The NCC-based nanocomposite hydrogel shows a clear inflexion point at about 100% strain, indicating transition from linear elastic to plastic response. This elastic-plastic behaviour indicates that the NCC-based nanocomposite hydrogels (1) have the ability to absorb a significant amount of energy (highly tough material), (2) are stiff (high modulus), and (3) have high tensile strength in the plastic range (over 7 times higher than the elastic range). This significant plastic response for NCC-based nanocomposite hydrogels is a unique feature made possible by the NCC reinforcing mechanism.

Figure 4:
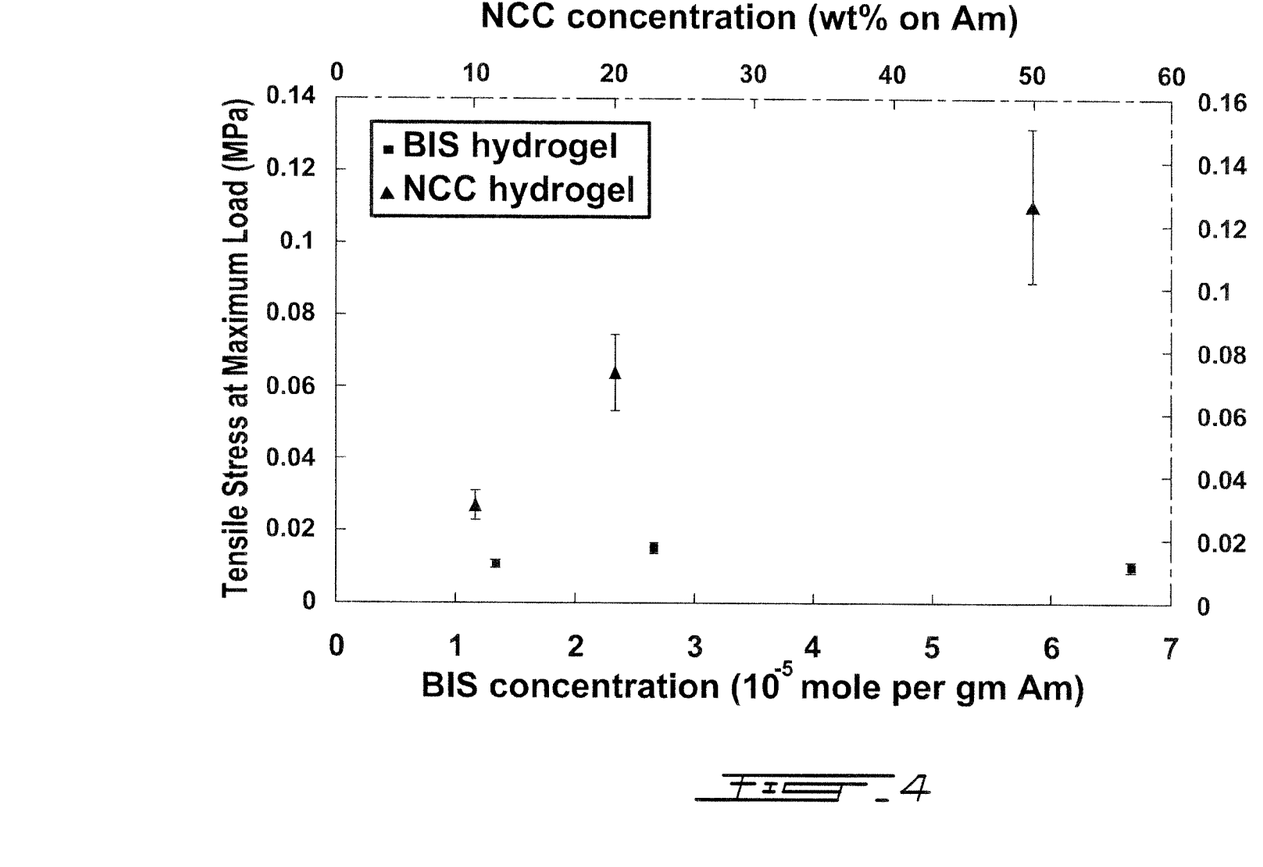
FIG. 4: is a plot showing the tensile strength response to increasing nanoreinforcement/crosslinker loading for NCC-based nanocomposite (solid triangle) and BIS-based (solid square) hydrogels.

FIG. 4 depicts the tensile strength response as a function of increasing NCC (or BIS) contents in NCC-based nanocomposite hydrogels, and hydrogels prepared using an organic crosslinker, respectively. It is evident that the tensile strength increases with increasing BIS content (solid squares), reaches a peak at ~0.015 MPa, then decreases. The tensile strength for the NCC-based nanocomposite hydrogel, however, increases steadily with increasing NCC content (solid triangles). For instance, at 50% w/w NCC loading on the monomer, the tensile strength reaches 0.126 MPa, more than 8 times higher than that for the regular hydrogel.

Example 3

Compression tests are carried out using a Thermal Mechanical Analyzer (TMA Q 400) under an expansion probe. The height of the sample is about 6 mm and the diameter of the probe is 2.795 mm. The measurement is done by applying an initial force of 0.01 N and a force ramp 0.1 N/min to 1.2 N. Compressions between 0.5 to 2.5 mm are used to calculate the compressive modulus.

Figure 5:
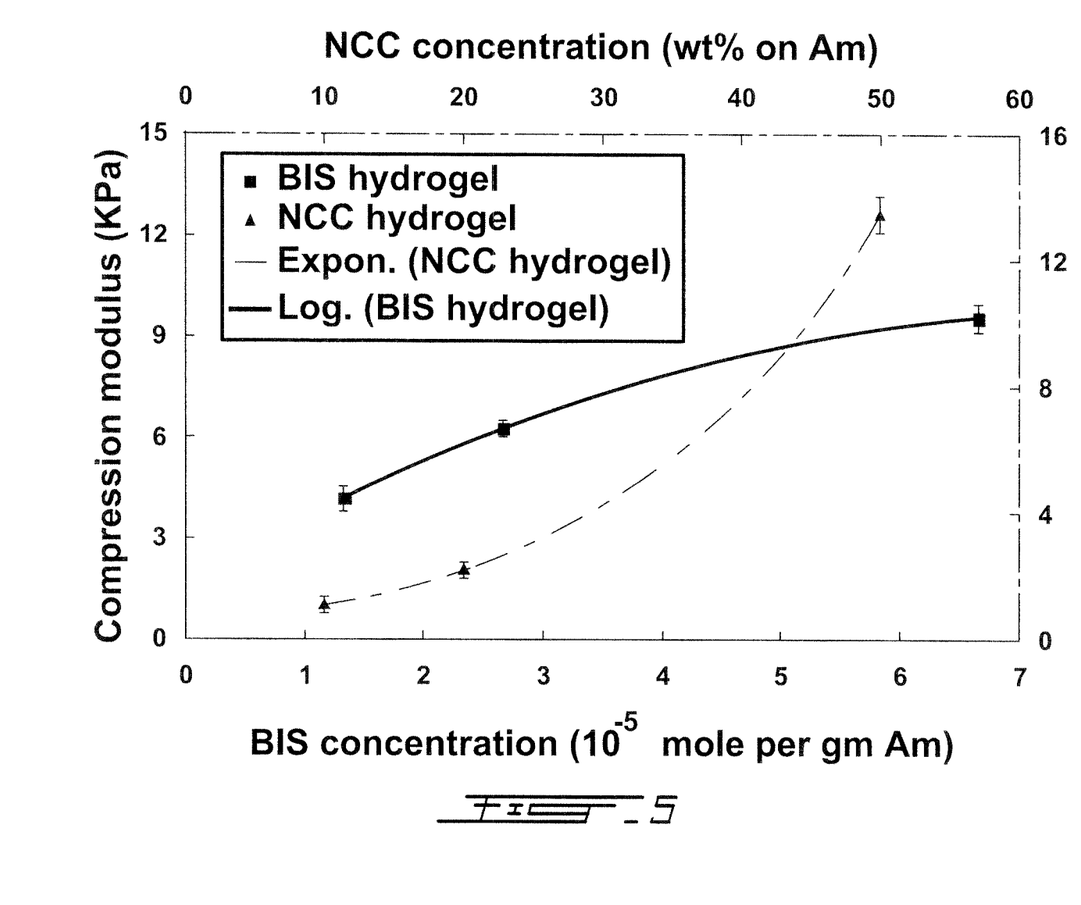
FIG. 5: is a plot showing the compression modulus as a function of nanoreinforcement/crosslinker loading for NCC-based nanocomposite (solid triangle) and BIS-based (solid square) hydrogels.

FIG. 5 depicts the compression modulus of the hydrogels as a function of crosslinking densities or NCC loading as weight percentage onto the monomer. For example, for the BIS hydrogel (solid squares) the compression modulus increases with increasing crosslinker concentration and the data follow a logarithm response levelling off at ~9 kPa. The compression modulus for the NCC-based nanocomposite hydrogel, however, exponentially increases with increasing NCC loading (solid triangles). The results also indicate that increasing modified NCC loading in the nanocomposite hydrogel will enhance the compression modulus at a much faster rate than in the case of BIS-based hydrogels.

Example 4

The swelling properties of the hydrogels are measured by soaking the prepared hydrogels in DI water for 3 days, and comparing the weights of the hydrogels before and after swelling. The swelling ratio is defined as the ratio of the weight after soaking to that before soaking. Table 2 clearly shows that the NCC nanocomposite hydrogels have higher swelling ratios than the regular hydrogels. It is also found that the swelling of the NCC-based nanocomposite hydrogels is reversible if dried and re-soaked in water.

REFERENCES

1. Yoshida, R., Design of functional polymer gels and their application to biomimetic materials. *Current Organic Chemistry* 2005, 9, (16), 1617-1641.
2. Tokarev, I.; Minko, S., Stimuli-responsive hydrogel thin films. *Soft Matter* 2009, 5, (3), 511-524.
3. Peppas, N. A.; Hilt, J. Z.; Khademhosseini, A.; Langer, R., Hydrogels in biology and medicine: From molecular principles to bionanotechnology. *Advanced Materials* 2006, 18, (11), 1345-1360.
4. Hoare, T. R.; Kohane, D. S., Hydrogels in drug delivery: Progress and challenges. *Polymer* 2008, 49, (8), 1993-2007.
5. Richter, A.; Paschew, G.; Klatt, S.; Lienig, J.; Arndt, K. F.; Adler, H. J. P., Review on hydrogel-based pH sensors and microsensors. *Sensors* 2008, 8, (1), 561-581.
6. He, C. L.; Kim. S. W.; Lee, D. S., In situ gelling stimuli-sensitive block copolymer hydrogels for drug delivery. *Journal of Controlled Release* 2008, 127, (3), 189-207.
7. Calvert, P., Hydrogels for Soft Machines. *Advanced Materials* 2009, 21, (7), 743-756.
8. Okumura, Y.; Ito, K., The polyrotaxane gel: A topological gel by figure-of-eight cross-links. *Advanced Materials* 2001, 13, (7), 485-+.
9. Haraguchi, K. Nanocomposite hydrogels. *Current Opinion in Solid State & Materials Science* 2007, 11, (3-4), 47-54.
10. Gong, J. P.; Katsuyama, Y.; Kurokawa, T.; Osada, Y., Double-network hydrogels with extremely high mechanical strength. *Advanced Materials* 2003, 15, (14), 1155-+.
11. Haraguchi, K.; Takehisa, T.; Fan, S., Effects of clay content on the properties of nanocomposite hydrogels composed of poly(N-isopropylacrylamide) and clay. *Macromolecules* 2002, 35, (27), 10162-10171.

The invention claimed is:

1. A nanocomposite hydrogel comprising a hydrophilic polymer derived from polymerization of a hydrophilic vinyl monomer and crosslinked by a crosslinker comprising nanocrystalline cellulose (NCC), wherein said crosslinker comprises a modified NCC in which a modifier has a first functional group coupled with a hydroxyl group of the NCC, and a second functional group coupled to said polymer, wherein said second functional group is a vinyl group, each particle of said NCC being coupled to the first functional group of at least two units of the modifier to provide crosslinking of said hydrophilic polymer by said particle, said hydrophilic polymer comprising a plurality of vinyl polymer chains, each chain extending between a pair of spaced apart NCC particles; and each said particle of said NCC having a cross-section of 5-10 nm and a length of 20-100 nm.

2. A nanocomposite hydrogel according to claim 1, wherein said hydrophilic polymer is a homopolymer derived from homopolymerization of said hydrophilic vinyl monomer.

3. A nanocomposite hydrogel according to claim 1, wherein said hydrophilic polymer is derived from copolymerization of a hydrophilic vinyl monomer and a comonomer for said hydrophilic vinyl monomer.

4. A nanocomposite hydrogel according to claim 3, wherein said comonomer is a hydrophilic comonomer.

5. A nanocomposite hydrogel according to claim 1, wherein said hydrophilic monomer is selected from acrylic acid, acrylamide (AM), vinylpyrrolidone, N-isopropylacrylamide (NIPAM), and N-vinylformamide (NVF).

6. A nanocomposite hydrogel according to claim 1, wherein said modifier is a vinyl monomer having a functional group.

7. A nanocomposite hydrogel according to claim 1, wherein said modifier is selected from the group consisting of glycidyl methacrylate, trimethylsilyl methacrylate,
- 2-(trimethylsilyloxy)ethyl methacrylate, 2-aminoethyl methacrylate,
- 2-isocyanatoethyl methacrylate, 2-chloroethyl acrylate, 3-(trimethoxysilyl)propyl acrylate, glycidyl acrylate, vinyl isocyanate, 2-aminoethyl vinyl ether, and vinyltrimethoxysilane.

8. A nanocomposite hydrogel according to claim 6, wherein said vinyl monomer having a functional group is glycidyl methacrylate.

9. A method of preparing a nanocomposite hydrogel comprising: polymerizing a hydrophilic vinyl monomer to form a hydrophilic polymer in the presence of a crosslinker for said polymer, which crosslinker comprises nanocrystalline cellulose (NCC), whereby said hydrophilic polymer is crosslinked by said crosslinker, wherein said crosslinker comprises a modified NCC in which a modifier has a first functional group coupled with a hydroxyl group of the NCC, and a second functional group coupled to said polymer, wherein said second functional group is a vinyl group, each particle of said NCC being coupled to the first functional group of at least two units of the modifier to provide crosslinking of said hydrophilic polymer by said particle, said hydrophilic polymer comprising a plurality of vinyl polymer chains, each chain extending between a pair of spaced apart NCC particles; and each said particle of said NCC having a cross-section of 5-10 nm and a length of 20-100 nm.

10. A method according to claim 9, wherein said hydrophilic monomer is a hydrophilic vinyl monomer.

11. A method according to claim 9, wherein said polymerizing comprises copolymerization of said hydrophilic monomer and a comonomer.

12. A method according to claim 11, wherein said comonomer is a hydrophilic comonomer.

13. A method according to claim 9, wherein said crosslinker comprises NCC modified with a modifier having first and second functional groups, reacting said first functional group with a hydroxyl group of the NCC, and coupling said second functional group to the polymer.

14. A method according to claim 13, wherein said hydrophilic monomer is selected from acrylic acid, acrylamide (AM) and vinylpyrrolidone, N-isopropylacrylamide (NIPAM), and N-vinylformamide (NVF).

15. A method according to claim 13, wherein said modifier is selected from the group consisting of glycidyl methacrylate, trimethylsilyl methacrylate,
- 2-(trimethylsilyloxy)ethyl methacrylate, 2-aminoethyl methacrylate,
- 2-isocyanatoethyl methacrylate, 2-chloroethyl acrylate, 3-(trimethoxysilyl)propyl acrylate, glycidyl acrylate, vinyl isocyanate, 2-aminoethyl vinyl ether, and vinyltrimethoxysilane.

16. A method according to claim 13, wherein said modifier is a vinyl monomer having a functional group.

17. A method according to claim 16, wherein said vinyl monomer having a functional group is glycidyl methacrylate.

18. A medical device formed from the nanocomposite hydrogel of claim 1.

19. An absorbent hygiene device formed from the nanocomposite hydrogel of claim 1.

20. The medical device of claim 18, selected from a drug delivery system for medical applications; a stimuli-responsive sensor, a medical implant and a tissue engineered material.

* * * * *